(12) United States Patent
Emodi

(10) Patent No.: US 10,070,848 B2
(45) Date of Patent: Sep. 11, 2018

(54) INTRACAVITY ILLUMINATION DEVICE

(71) Applicant: Omri Emodi, Zychron Yacov (IL)

(72) Inventor: Omri Emodi, Zychron Yacov (IL)

(*) Notice: Subject to any disclaimer, the term of this patent is extended or adjusted under 35 U.S.C. 154(b) by 0 days.

(21) Appl. No.: 14/439,437

(22) PCT Filed: Nov. 6, 2013

(86) PCT No.: PCT/IL2013/050915
§ 371 (c)(1),
(2) Date: Apr. 29, 2015

(87) PCT Pub. No.: WO2014/072976
PCT Pub. Date: May 15, 2014

(65) Prior Publication Data
US 2015/0272693 A1 Oct. 1, 2015

Related U.S. Application Data

(60) Provisional application No. 61/724,044, filed on Nov. 8, 2012.

(51) Int. Cl.
*A61B 1/06* (2006.01)
*A61B 17/00* (2006.01)
(Continued)

(52) U.S. Cl.
CPC ............... *A61B 17/00* (2013.01); *A61B 1/24* (2013.01); *A61B 90/30* (2016.02); *A61B 90/50* (2016.02);
(Continued)

(58) Field of Classification Search
CPC .......................................... A61B 1/06–1/0653
(Continued)

(56) References Cited

U.S. PATENT DOCUMENTS 1,036,497 A * 8/1912 Krebs ...................... A61B 1/24
600/237
1,094,575 A * 4/1914 Jouthas .............. A61B 17/0206
600/219
(Continued)

FOREIGN PATENT DOCUMENTS

CN 101605506 12/2009
CN 201803114 4/2011
(Continued)

OTHER PUBLICATIONS

International Search Report, dated Feb. 9, 2014. appl. No. 2013050915.

*Primary Examiner* — Eduardo C Robert
*Assistant Examiner* — Michelle C Eckman
(74) *Attorney, Agent, or Firm* — Browdy and Neimark, P.L.L.C.

(57) ABSTRACT

The present invention relates to an intracavity system and method for illuminating a surgical site within a body cavity to be used with a stationary surgical device. The system comprises at least one light source comprising a light-emitting diode configured and operable to emit illumination light into the body cavity. The light-emitting diode is mounted on a coupling assembly for securing the light-emitting diode to an external surface of the stationary surgical device to permit selectively fastening the light source to any desired location along the stationary surgical device and repositioning thereof. Each of the at least one light source is connected via a wire to a handheld self-contained electrical power supply unit. The wire is configured to transmit power supply energy from the power supply unit to the light source.

11 Claims, 3 Drawing Sheets

(51) Int. Cl.
*A61B 1/24* (2006.01)
*A61B 90/30* (2016.01)
*A61B 90/50* (2016.01)
*A61B 90/57* (2016.01)

(52) U.S. Cl.
CPC ....... *A61B 1/06* (2013.01); *A61B 2017/00876* (2013.01); *A61B 2090/309* (2016.02); *A61B 2090/571* (2016.02); *A61B 2560/0214* (2013.01)

(58) Field of Classification Search
USPC .......... 600/199, 223, 245, 249; 362/572–573
See application file for complete search history.

(56) References Cited

U.S. PATENT DOCUMENTS

| | | | | |
|---|---|---|---|---|
| 1,122,086 A * | 12/1914 | Dunlop | ................. | A61C 1/088 433/29 |
| 1,143,515 A * | 6/1915 | Dunlop | ................. | A61B 1/24 433/139 |
| 1,706,500 A * | 3/1929 | Smith | ................. | A61B 17/02 600/232 |
| 2,075,534 A * | 3/1937 | McCormack | ................. | A61B 1/24 600/219 |
| 2,411,568 A * | 11/1946 | Foote | ................. | F21V 33/0068 313/1 |
| 2,528,458 A * | 10/1950 | Stone | ................. | A61B 1/24 600/212 |
| 2,800,896 A * | 7/1957 | Thum | ................. | A61B 1/24 362/84 |
| 3,895,624 A * | 7/1975 | Georgiade | ................. | A61F 5/00 600/237 |
| 3,916,880 A * | 11/1975 | Schroer | ................. | A61B 1/24 600/205 |
| 3,927,664 A * | 12/1975 | Georgiade | ................. | A61C 7/10 600/237 |
| 4,562,832 A * | 1/1986 | Wilder | ................. | A61B 1/32 138/DIG. 8 |
| 4,592,344 A * | 6/1986 | Scheer | ................. | A61B 1/07 433/29 |
| 4,619,249 A * | 10/1986 | Landry | ................. | A61B 5/0059 362/199 |
| 4,627,421 A * | 12/1986 | Symbas | ................. | A61B 17/0206 600/232 |
| 4,729,070 A * | 3/1988 | Chiu | ................. | F21V 17/02 362/227 |
| 4,991,566 A * | 2/1991 | Shulman | ................. | A61B 1/24 433/7 |
| 5,054,906 A * | 10/1991 | Lyons, Jr. | ................. | A61B 3/0008 351/205 |
| 5,199,418 A * | 4/1993 | Jamison, Jr. | ................. | A61B 1/0676 362/205 |
| 5,353,786 A * | 10/1994 | Wilk | ................. | G02B 6/0005 362/219 |
| 5,462,435 A * | 10/1995 | Young | ................. | A61B 1/07 433/140 |
| 5,569,300 A * | 10/1996 | Redmon | ................. | A61B 17/0206 600/219 |
| 6,379,296 B1 * | 4/2002 | Baggett | ................. | A61B 1/303 600/178 |
| 6,428,180 B1 * | 8/2002 | Karram | ................. | A61B 5/0059 362/109 |
| 6,974,321 B2 * | 12/2005 | Hirsch | ................. | A61C 5/14 433/140 |
| 7,287,981 B2 * | 10/2007 | Hirsch | ................. | A61C 1/088 433/29 |
| 7,972,024 B2 * | 7/2011 | Deleeuw | ................. | F21V 21/0885 362/103 |
| 8,021,148 B2 * | 9/2011 | Goodson | ................. | A61C 1/088 433/29 |
| 8,348,838 B1 * | 1/2013 | Khurgin | ................. | A61M 1/008 600/212 |
| 2001/0008752 A1 * | 7/2001 | Hirsch | ................. | A61B 1/24 433/29 |
| 2003/0095781 A1 * | 5/2003 | Williams | ................. | A61B 17/02 385/146 |
| 2004/0063060 A1 * | 4/2004 | Meyers | ................. | A61C 1/088 433/29 |
| 2004/0242970 A1 * | 12/2004 | Burns | ................. | A61B 1/2673 600/238 |
| 2006/0063979 A1 * | 3/2006 | Rosenblood | ................. | A61B 1/0669 600/237 |
| 2006/0069316 A1 * | 3/2006 | Dorfman | ................. | A61C 5/14 600/237 |
| 2006/0155171 A1 * | 7/2006 | Yang | ................. | A61B 1/0676 600/238 |
| 2006/0224045 A1 * | 10/2006 | Whipple | ................. | A61B 17/3421 600/245 |
| 2006/0256575 A1 * | 11/2006 | Vayser | ................. | A61B 1/0623 362/573 |
| 2007/0060795 A1 * | 3/2007 | Vayser | ................. | A61B 1/32 600/245 |
| 2007/0066872 A1 * | 3/2007 | Morrison | ................. | A61B 17/02 600/212 |
| 2007/0156022 A1 * | 7/2007 | Patel | ................. | A61B 1/267 600/199 |
| 2007/0156028 A1 * | 7/2007 | Van Lue | ................. | A61B 1/24 600/237 |
| 2008/0096165 A1 * | 4/2008 | Virnicchi | ................. | A61B 1/00096 433/140 |
| 2008/0145813 A1 * | 6/2008 | Crohn | ................. | A61B 1/247 433/29 |
| 2008/0266840 A1 | 10/2008 | Nordmeyer et al. | | |
| 2009/0323370 A1 * | 12/2009 | Koo | ................. | A61B 1/00034 362/573 |
| 2010/0125172 A1 * | 5/2010 | Jayaraj | ................. | A61B 1/06 600/249 |
| 2010/0203466 A1 | 8/2010 | Lawrence | | |
| 2010/0274097 A1 * | 10/2010 | Cho | ................. | A61B 17/0206 600/249 |
| 2010/0317928 A1 * | 12/2010 | Subramaniam | ................. | A61B 17/0206 600/245 |
| 2011/0004068 A1 * | 1/2011 | Bruto Da Costa | ................. | A61B 90/36 600/249 |
| 2011/0028792 A1 * | 2/2011 | Ibrahim | ................. | A61B 17/02 600/205 |
| 2011/0060192 A1 * | 3/2011 | Pastron | ................. | A61M 16/0463 600/205 |
| 2012/0015320 A1 | 1/2012 | Koo | | |
| 2012/0040305 A1 | 2/2012 | Karaivan et al. | | |
| 2012/0228528 A1 * | 9/2012 | Koo | ................. | A61B 1/0669 250/504 R |
| 2012/0241188 A1 * | 9/2012 | Power | ................. | A61B 1/00087 174/68.3 |
| 2013/0066153 A1 * | 3/2013 | McGrath | ................. | A61B 1/00034 600/188 |
| 2013/0197313 A1 * | 8/2013 | Wan | ................. | A61B 1/32 600/202 |
| 2013/0197317 A1 * | 8/2013 | Daniel | ................. | A61B 1/0684 600/249 |
| 2013/0204094 A1 * | 8/2013 | Fiebel | ................. | A61B 1/0692 600/249 |
| 2013/0215383 A1 * | 8/2013 | Siminou | ................. | A61B 3/14 351/206 |
| 2014/0133173 A1 * | 5/2014 | Vayser | ................. | A61B 17/0206 362/572 |
| 2014/0275792 A1 * | 9/2014 | Hawkins | ................. | A61B 17/02 600/202 |
| 2014/0309500 A1 * | 10/2014 | Thompson | ................. | A61B 17/0206 600/219 |
| 2014/0343366 A1 * | 11/2014 | Coe | ................. | A61B 17/0293 600/205 |
| 2015/0250555 A1 * | 9/2015 | Haverich | ................. | A61B 19/5202 600/245 |

(56) References Cited

U.S. PATENT DOCUMENTS

2015/0265387 A1* 9/2015 Alexander ......... A61B 17/3468
600/37

FOREIGN PATENT DOCUMENTS

| KR | 20110083836 A | 7/2011 |
|----|---------------|--------|
| MX | 2009012827 A | 5/2011 |
| WO | 0152720 A1 | 7/2001 |
| WO | 0207632 A1 | 1/2002 |
| WO | 2009070815 A2 | 6/2009 |
| WO | 2011065707 A2 | 6/2011 |

* cited by examiner

INTRACAVITY ILLUMINATION DEVICE

TECHNOLOGICAL FIELD

The present invention relates in general, to surgical and dental appliances, and, in particular, to surgical appliances for illuminating body cavities of patient for examination and/or operative purposes.

References considered to be relevant as background to the presently disclosed subject matter are listed below:
  WO 11/65707
  US 2001/008752
  US 2004/063060
  US 2009/323370
  US 2008/145813
  US 2012/015320
  MX 2009/012827
  U.S. Pat. No. 8,021,148
Acknowledgement of the above references herein is not to be inferred as meaning that these are in any way relevant to the patentability of the presently disclosed subject matter.

BACKGROUND OF THE INVENTION

Various techniques have been developed for illuminating a patient's cavities for performing a medical examination or for performing operations therein. Typically, the interior part of the surgical site is illuminated by a light source mounted at a certain distance above the surgical bed/chair within which the patient lays/sits. Usually, three different spot lights are attached to the roof of the operation room, each of them being manually manipulated during surgery. The spot can be focused via the handle of the operation light, if at all. However, the amount of light entering the surgical or examination site is limited, first due to the fact that the light source is remote from the patient's body, further, the surgeon often positions himself or his instruments between the light source and the patient's cavity in order to properly view into the patient's mouth, thus blocking light from entering the surgical cavity. Numerous devices have been developed to overcome this problem.

GENERAL DESCRIPTION

The present invention describes an intracavity illumination device for illuminating the interior cavity of a patient's surgical site during a medical procedure that eliminates the problems associated with restricted illuminated field of view as mentioned above. In this connection, it should be noted that operation light is an essential element for visualization of surgical sites and that an optimal light should be provided during surgery.

During surgery, the surgeon has to readjust the lights to the area on which he is working. This takes time and the surgeon is distracted from the surgical field till the light is perfectly adjusted. This manipulation may take time and irritate the surgeon, and during manipulation the light handle may be desterilized. Moreover, operating with several surgeons may create a situation in which one of the surgeons blocks the light and the area of the operation is under shadow. During surgery, it is sometimes necessary to change the patient's position or operate on different sites simultaneously. This requires a manual change of position of the operation light and reduces the amount of light due to distribution of the light source to several areas. The arms of the light source may sometimes be rigid and change position after being placed in the surgical site. Furthermore, if the patient changes his body's position during the operation, which occurs often, a readjustment of the light source is required.

Moreover, by using the illumination techniques known in the art, deep cavities of the patient's body are illuminated with a narrow field of view. In deep cavities, the light source is usually distributed equally while the surgeon needs a direct focused light on the operated site. The light is usually scattered by metal retractors and different surgical instruments. Deep body cavities have dark areas due to poor penetration of light.

Headlight systems have been developed to try to overcome such drawbacks. In such systems, light can be worn on the head of each surgeon, illuminating the operating area. This system requires an accurate adjustment prior to surgery and may change its position due to head movement of the surgeon. During surgery, this source of light has to be manually continually adjusted relatively to the surgeon's position in order to produce the required amount of light in the surgical site. This manipulation may cause contamination of the surgical field due to the handle being unsterilized. Moreover, the headlight weighs on the surgeon's head, is uncomfortable and creates a warm environment, sometimes causing the surgeon to sweat. Furthermore in such systems, the light source on the surgeon's head is usually connected via a fiber optics cable to a stand carrying the power source. All these elements restrict the surgeon's movement and also limit a change of position of the other surgeons during the operation.

Therefore, there is a need in the art in facilitating illumination of the interior cavity of a patient's surgical site during a medical procedure, by providing an intracavity light-emitting diode (LED)-based system which is on the one hand an autonomous mobile system in that it has no wire connectors to any stationary bulk external power supply and on the other hand is configured to be easily attachable/detachable to/from surgical retractors or other commonly used surgical devices.

In this connection, it should be noted that some devices such as, as described for example in US 2011/004068, have been developed in which an illumination apparatus is attached to various surgical instruments, one at a time, during the operation. The light source is placed in close proximity to the tip of the surgical instrument, such as surgical scissors, that the surgeon is handling. However, it should be understood that the surgical instrument is moving during the operation continually displacing the light source as well as disturbing the precise operation of the surgical instrument. The surgical instrument is more complicated to manipulate reducing the control of the surgeon. Moreover, when the surgeon changes from one surgical instrument to another, the external illumination apparatus has to be displaced and repositioned even if it is not needed.

The present invention provides an intracavity system for illuminating a surgical site within a body cavity to be used with a stationary surgical device. The system comprises at least one light source comprising a light-emitting diode configured and operable to emit illumination light into the body cavity. The light source is mounted on a coupling assembly configured for securing the light-emitting diode to an external surface of the stationary surgical device to permit selectively fastening the light source to any desired location along the stationary surgical device and repositioning the light source, if needed. Each of the at least one light source is connected via a wire to a handheld self-contained electrical power supply unit. In some embodiments, the electrical power supply unit may be configured to extend outside of the body cavity when the light source is in the body cavity. Alternatively, both, the light source and the electrical power supply unit may be configured to be positioned inside the body cavity. The wire is configured to transmit power supply energy from the power supply unit to the light source. The stationary surgical device comprises at least one of a bite piece and a retractor adapted to be engaged within the body cavity. Thus, the intracavity LED-based system of the invention is configured such that each LED can be attached to any desired location along the stationary surgical device e.g. a retractor. The retractor can either actively separate the edges of a surgical incision or wound, or can hold back underlying organs and tissues, so that body parts under the incision may be accessed. More specifically, the attachment is preferably done via magnetic elements associated with the LEDs, or generally via a glue material which is easily convertible between its gluing and non-gluing states. In some embodiments, each of the at least one light source is coated with an adhesive material enabling to temporarily affix the least one light source to the stationary surgical device. Both of these options provide desirably strong attachment as well as an easy detachment of the LED from the retractor in addition to a movement of the LED to another portion on the retractor. Therefore, the coupling assembly comprises at least one of a magnetic, a clipping and a notch element configured to be coupled to the stationary surgical device.

In some embodiments, each of the at least one light-emitting diode is separately operable. Moreover, each of the at least one light-emitting diode may have a different physical orientations so as to emit in a wide range of directions. Each of the at least one light source may comprise a dimmer providing a different shade of light and optimizing the illumination of the surgical site.

The system of the present invention may also be used for illuminating intubation operations in which the accessibility and the field of view are particularly limited. Moreover, the system is easy to manipulate, comfortable for the surgeon and can be sterilized. In some embodiments, the wire is of a predetermined length to enable a compact configuration of the system.

In some embodiments, at least one light-emitting diode, the coupling assembly and the wire are silicon coated. The at least one light-emitting diode, the coupling assembly and the wire are therefore sterilizable.

In other embodiments, at least one light-emitting diode, the coupling assembly and the wire are coated with a radiopaque material preventing the passage of X rays, such that these elements can be easily located within the cavity even if they are displaced out of the field of view of the surgeon.

In some embodiments, the power supply unit comprises a rechargeable battery and the wire is connected to the poles of the rechargeable battery.

In some embodiments, the coupling assembly comprises two spaced-apart magnetic elements of opposite magnetic polarity. A first magnetic element is configured to be fastened to the light source and a second magnetic element is configured to be mounted on the external surface of the surgical device. The two spaced-apart magnetic elements may be connected via a wire.

In some embodiments, the electrical power supply unit comprises a power source and a magnetic element configured for securing the power supply unit to any portion of an external surface of the stationary surgical device.

In some embodiments, the electrical power supply unit is silicon coated.

There is also provided a method for illuminating a surgical site within a body cavity to be used with a stationary surgical device. The method comprises coupling between at least one light source comprising a light-emitting diode configured and operable to emit illumination light into the body cavity and a coupling assembly for securing the light-emitting diode to an external surface of the stationary surgical device to permit selectively fastening the light source to any desired location along the stationary surgical device and repositioning thereof. The coupling may comprise at least one of magnetically coupling, and mechanically coupling.

In some embodiments, the coupling comprises coating the at least one light source with an adhesive material enabling to temporarily affix the least one light source to the stationary surgical device.

In some embodiments, the method comprises separately operating each of the at least one light-emitting diode to provide a different shade of light and optimize the illumination of the surgical site. While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

BRIEF DESCRIPTION OF THE FIGURES

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
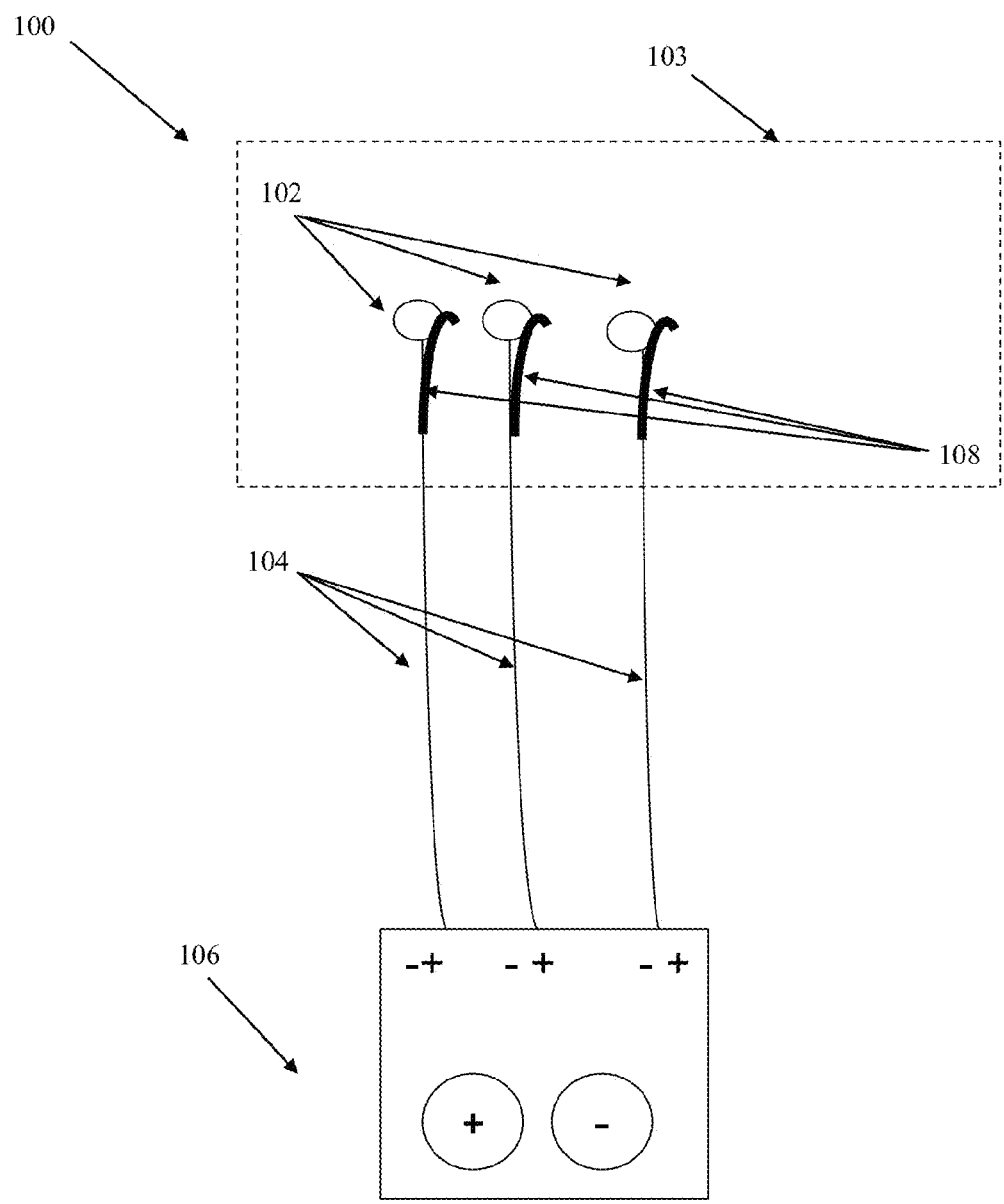
FIG. 1 schematically illustrates a non-limiting example of the system of the present invention for illuminating a surgical site within a body cavity to be used with a stationary surgical device.

Reference is made to FIG. 1, representing a general schematic representation of a non-limiting example of an intracavity system 100 of the present invention. The intracavity system 100 comprises at least one light source 103 comprising a light-emitting diode 102 configured and operable to emit illumination light into a cavity of a patient, the light-emitting diode 102 is mounted on a coupling assembly 108 for securing the light-emitting diode 102 to an external surface of a stationary surgical device (any surgical retractor as shown for example in FIG. 2) to permit selectively fastening the light source 103 to any desired location along the stationary surgical device and repositioning thereof. Each light source 103 is connected via a wire 104 to a handheld self-contained electrical power supply unit 106. In some embodiments, the power supply unit 106 is configured to extend outside of the body cavity when the light source 103 is in the body cavity. Alternatively, both, the light source 103 and the electrical power supply unit 106 may be configured to be positioned inside the body cavity. The wire 104 is used to transmit power supply energy from the power supply unit 106 to the light source 103. Therefore, there is provided an intracavity LED-based system having a flexible light source. In this non-limiting example, three autonomic LEDs 102 are attached to wires 104, connecting between the LEDs 102 and a rechargeable and portable unit 106. Every LED 102 has been controlled to produce different shades of bright light to create an optimal lighting inside the surgical site without any external interference. In this non-limiting example, the three LEDs are attached with a small strip of magnets 108 to a surgical stationary device such as a surgical retractor.

The coupling assembly according to the present invention may be at least one magnet, since the magnetic properties of magnets make them easy to attach and remove from surgical devices, the vast majority of which are metallic. Magnetic mounting of the LED to the device is advantageous as it allows for optimal positioning of the LED on the device. In this connection, it should be noted that, in some embodiments, the coupling assembly may be a single magnetic element to be magnetically coupled to a metallic surgical devices. However, the present invention also provides the possibility of a magnetic coupling of the light source to any surgical device, even if the surgical device is non-metallic. In this non-limiting example, the coupling assembly comprises two spaced-apart magnetic elements of opposite magnetic polarity. The first magnetic element may be fastened to the light source and the second magnetic element may be mounted on the external surface of the non-metallic surgical device turning the surgical device to be magnetically attracted. In this way, the magnetized light source and the second magnetic element are positioned at the opposite sides of any portion of the surface of a stationary surgical device such that the light source can be positioned at any desirable location along the magnetized non-metallic surgical device. In some embodiments, the two magnetic elements are connected via a wire to prevent the loss or the search of the second magnetic element within the body cavity.

Moreover, also not shown, the coupling assembly may be a clip attachment or any other means which allows easy attachment and detachment. Such a coupling assembly may also include the use of an adhesive to temporarily affix the LED to the surgical device. The magnets 108 must be sufficiently strong to ensure that the light source 103 does not fall off during normal use and also not so strong that it prevents the surgeon from being able to shift the light source 103 on the surgical device, should it be necessary.

Although other light sources are possible, provided they do not put the patient's health or the operation at risk, the LEDs have the advantage of being very small (usually less than 8 mm), emitting very little heat and have excellent longevity and durability characteristics. The LED system is also not sensitive to temperature. Moreover, most LED-based systems, "Class I LED products", are safe under all conditions of normal use. The emitted light is much stronger per watt than incandescent light bulbs and the intensity of light is independent on the size or the external form of the LED. The LED can emit different shades of light by using a dimmer. Moreover, to be activated, the LED requires small power. The LEDs 102 is connected in the usual fashion to power supply unit 106. The connection between the LED 102 and the power supply unit 106 is provided by wiring and contacts as is well known in the field of electrical engineering. A switch may or may not be incorporated in the wiring in order to make it possible to turn on and off the LEDs 102.

The power supply unit 106 has also a reduced size is portable and can be clipped on the surgeon's clothes.

It should be noted that the wires 104 have a predefined length in the range of 6-10 cm and even more, such that the system 100 is compact and has a reduced size. In some embodiments, the whole LED-based system 100 including the magnets and wires are silicon coated. The LED-based system can be sterilized and withstands humidity, heat and cold. It is a flexible system. The magnets attach the LED and wires to the surgical devices so they will not interfere with surgery. The system does not require space and is not connected to an external electrical source during surgery. It is easy to manipulate and may be used under any condition: field hospital, operation room, out-clinic, private clinic and emergency settings, where there is no electrical source to connect to.

Figure 2:
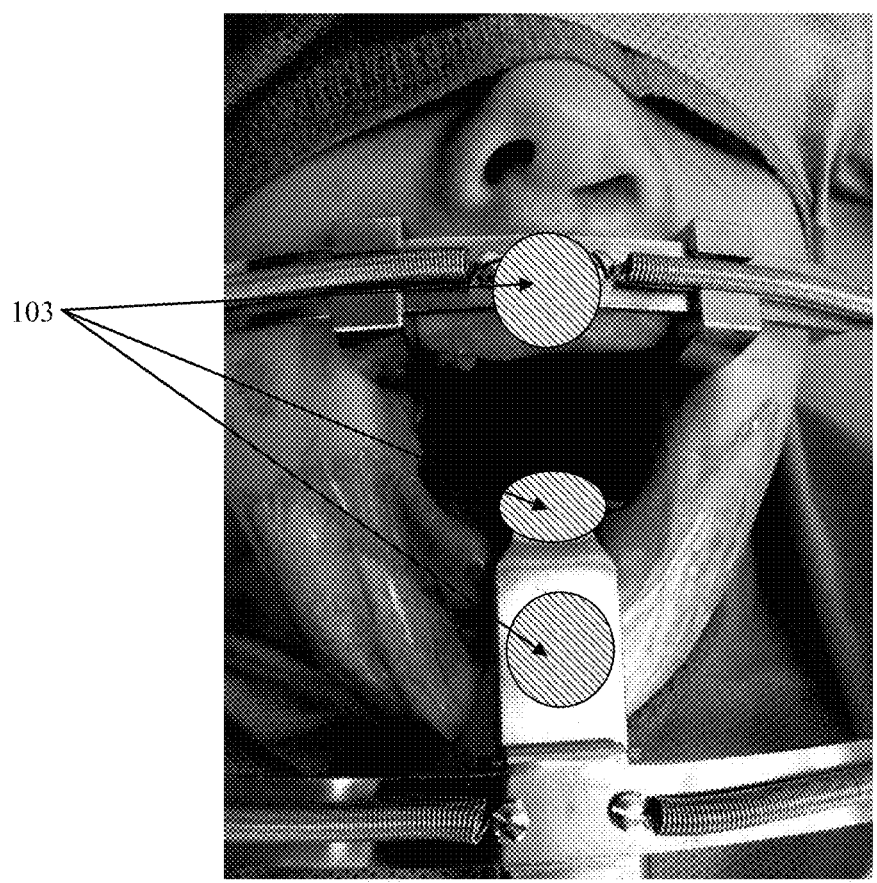
FIG. 2 is picture of an oral Digman retractor to be used with the system of the present invention; and, FIG. 3 schematically illustrates another embodiment of the system of the present invention for illuminating a surgical site within a body cavity to be used with a stationary surgical device.

Reference is made to FIG. 2 illustrating an intraoral Digman retractor to be used with the system of the present invention. A plurality of light sources 103 are attached to the bite piece and adjusted according to the surgical site to be operated. In this connection, it should be noted, that the system of the present invention is adaptable to standard existing surgical devices. The present invention, by using magnets as coupling assembly, allows the surgeon to easily magnetically attach the light source to a certain stationary surgical device such as a bite piece or a retractor, without manufacturing specifically designed surgical instruments. The surgeon can also shift and adjust the angle of the light by repositioning the light source on the device. For example, if the surgeon requires a more intense light on a certain area, he can easily slide the light source down the surface of the surgical device so that the light source is closer to the targeted area. Moreover, the surgeon may also control independently the intensity of each light source in the plurality of light sources 103 according to his needs. This leads to more control and an improvement to existing surgical techniques. When the surgeon switches to another surgical site he can easily remove the light source and magnetically re-attach it to another place along the device and so forth. The ability of the surgeon to do these exchanges himself instead of relying on others also results in the simplification of procedures in the operating room. They can be easily removed and re-attached.

Figure 3:
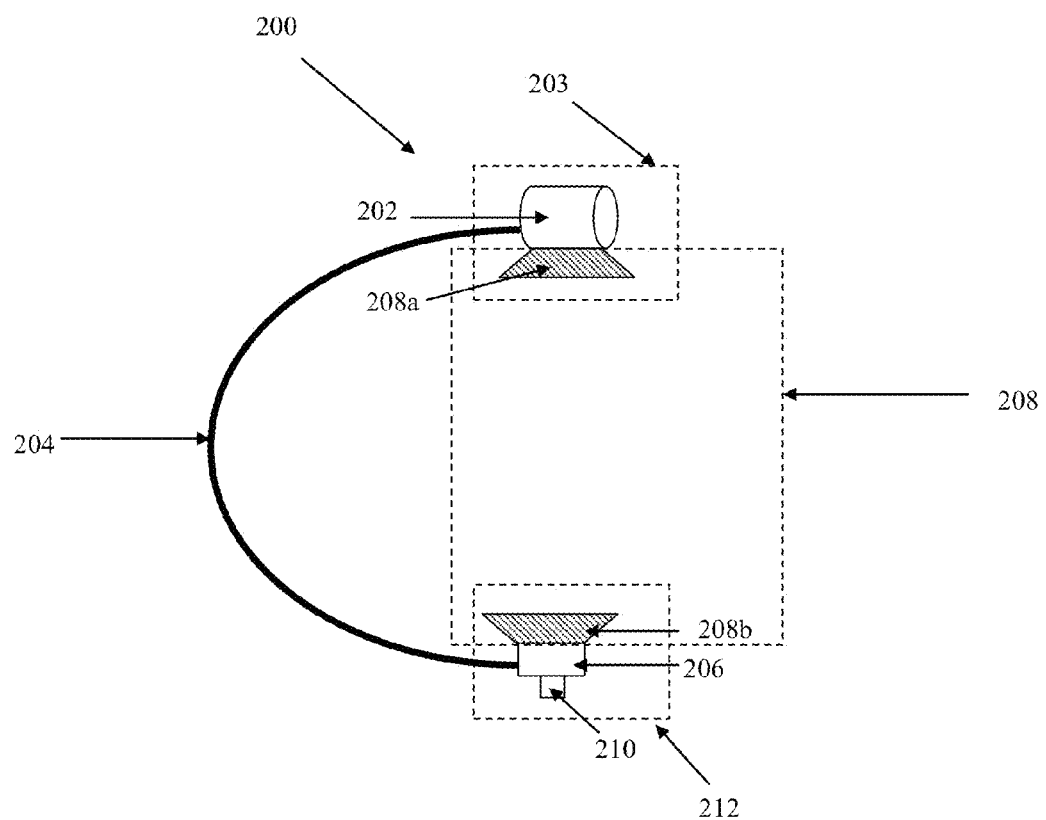

Reference is made to FIG. 3 illustrating another embodiment of the intracavity system 200 of the present invention. The intracavity body system 200 comprises at least one light source 203 comprising a light-emitting diode 202 configured and operable to emit illumination light into a cavity of a patient. A coupling assembly 208 is provided for selectively fastening the light source 103 to any desired location along a stationary surgical device and repositioning thereof. In this non-limiting example, the coupling assembly 208 comprises two spaced-apart magnetic elements 208a and 208b of opposite magnetic poles, each being positioned at the opposite sides of any portion of the surface of a stationary surgical device. By the way of magnetic attraction, the light-emitting diode 202 being mounted on one magnetic element 208a is secured to an external surface of a stationary surgical device being coupled to the other magnetic element 208b. This configuration permits selectively fastening the light source 203 to any desired location along a stationary surgical device even if the stationary surgical device is not made from a metallic material, and repositioning thereof.

In some embodiments, the electrical power is provided to the light source 203 via a wire 204 by a self-contained electrical power supply unit 212 comprising a power source 206 (e.g. battery) and a magnetic element 208b. The wire 204 is used to transmit power supply energy from the power supply source 206 to the light source 203, both of them being located inside the body cavity. In this non-limiting example, the wire 204 has a length in the range of 0.5-2 cm, providing a compact system. The magnetic element 208b is configured for securing the power supply unit 212 to any portion of an external surface of a stationary surgical device. In this connection, it should be noted that the magnetic element 208b may be used as a single element of the coupling assembly 208 or in addition to the magnetic element 208a depending on the material from which the stationary surgical device is formed. This configuration therefore provides an autonomous system for illuminating a body cavity during surgery. By using the system of the present invention, illumination of an open surgical site is provided for a long period of time (e.g. 5-6 hours) until the surgeon has finished his operation.

In some embodiments, the self-contained electrical power supply unit 212 may also comprise an on/off switch 210 for activating/deactivating the light source 203. The whole LED-based system 200, the light source 203, the coupling assembly 208, the wire 204 and the electrical power supply unit 212 may be silicon coated. Therefore, the present invention provides a new technique for illuminating a surgical area, reducing the distance between the light source and the surgical site and limits the interference between the spot light and the surgical site.

The invention claimed is:

1. A system for illuminating a surgical site within a body cavity, the system comprising:
   a plurality of autonomic light-emitting diodes (LED's) mounted on a coupling assembly, each LED comprising a first magnetic element, the light-emitting diode and the first magnetic element defining together a generally planar arrangement,
   wherein the magnetic element and the LED are on opposite sides of said arrangement such that, when in operation, each LED is selectively fastened onto an external surface of a stationary surgical device, wherein each LED is configured and operable to emit illumination light into said body cavity;
   and a plurality of electric wires, wherein each wire is configured to transmit power supply energy from an external power supply unit to a respective LED and enables different positioning and adjustment of each LED at a desired location onto an external surface of a stationary surgical device, forming in operation flexible light sources spaced-apart from each other.

2. The system of claim 1, wherein each of said at least one light-emitting diode is separately operable.

3. The system of claim 1, comprising a dimmer for controlling the light of one or more of the light-emitting diode.

4. The system of claim 1, wherein said wire being of a predetermined length enables a compact configuration of the system.

5. The system of claim 1, wherein said power supply unit comprises a rechargeable battery.

6. The system of claim 1, wherein said at least one light-emitting diode, said coupling assembly and said wire are silicon coated.

7. The system of claim 1, wherein said at least one light-emitting diode, said coupling assembly and said wire are sterilizable.

8. The system of claim 1, wherein the coupling assembly comprises a second magnetic element spaced-apart from said arrangement for fastening said arrangement to a non-magnetized surface.

9. The system of claim 8, wherein the second element is connected to said arrangement by a wire.

10. The system of claim 1, wherein said electric power supply unit comprises a power source and a magnetic element configured for securing said power supply unit to an external surface of a stationary surgical device.

11. The system of claim 10, wherein said electric power supply unit is sterilizable.

* * * * *